United States Patent
Lee et al.

(10) Patent No.: US 9,555,121 B2
(45) Date of Patent: Jan. 31, 2017

(54) COMPOSITION FOR FORMING COMPLEX, COMPLEX FORMED THEREFROM, AND COMPOSITION FOR ORAL ADMINISTRATION INCLUDING SAID COMPLEX

(71) Applicant: SAMSUNG FINE CHEMICALS CO., LTD., Ulsan (KR)

(72) Inventors: Sung Wan Lee, Incheon (KR); Jae Uk Cha, Seoul (KR); Jun Kee Hong, Yongin-si (KR); Hyon Ho Baek, Incheon (KR)

(73) Assignee: LOTTE FINE CHEMICAL CO., LTD., Ulsan (KR)

( * ) Notice: Subject to any disclaimer, the term of this patent is extended or adjusted under 35 U.S.C. 154(b) by 0 days.

(21) Appl. No.: 14/650,660

(22) PCT Filed: Dec. 10, 2013

(86) PCT No.: PCT/KR2013/011375
§ 371 (c)(1),
(2) Date: Jun. 9, 2015

(87) PCT Pub. No.: WO2014/092419
PCT Pub. Date: Jun. 19, 2014

(65) Prior Publication Data
US 2015/0335755 A1 Nov. 26, 2015

(30) Foreign Application Priority Data

Dec. 11, 2012 (KR) .................. 10-2012-0143828
Dec. 3, 2013 (KR) .................. 10-2013-0149471

(51) Int. Cl.
| | |
|---|---|
| A61K 31/35 | (2006.01) |
| A61K 47/38 | (2006.01) |
| A61K 47/46 | (2006.01) |
| A61K 47/02 | (2006.01) |
| A61K 47/48 | (2006.01) |
| A61K 9/48 | (2006.01) |
| A61K 31/045 | (2006.01) |
| A61K 31/235 | (2006.01) |
| A61K 31/353 | (2006.01) |
| A61K 31/355 | (2006.01) |
| A61K 31/375 | (2006.01) |
| A61K 36/53 | (2006.01) |
| C08L 1/02 | (2006.01) |
| A61K 47/22 | (2006.01) |

(52) U.S. Cl.
CPC ............ *A61K 47/38* (2013.01); *A61K 9/4808* (2013.01); *A61K 9/4866* (2013.01); *A61K 9/4891* (2013.01); *A61K 31/045* (2013.01); *A61K 31/235* (2013.01); *A61K 31/353* (2013.01); *A61K 31/355* (2013.01); *A61K 31/375* (2013.01); *A61K 36/53* (2013.01); *A61K 47/02* (2013.01); *A61K 47/46* (2013.01); *A61K 47/4823* (2013.01); *C08L 1/02* (2013.01); *A61K 47/22* (2013.01)

(58) Field of Classification Search
USPC .................. 514/456, 397; 424/729
See application file for complete search history.

(56) References Cited

U.S. PATENT DOCUMENTS

| | | | | |
|---|---|---|---|---|
| 6,299,925 | B1* | 10/2001 | Xiong | ........ A23F 3/30 426/285 |
| 9,198,946 | B2* | 12/2015 | Ogura | ........ A23F 3/163 |
| 2006/0002987 | A1 | 1/2006 | Bevacqua et al. | |
| 2006/0062881 | A1 | 3/2006 | Berndt | |
| 2009/0226547 | A1 | 9/2009 | Gilbard et al. | |
| 2011/0300241 | A1* | 12/2011 | Hsu | ........ A61K 31/35 424/729 |

FOREIGN PATENT DOCUMENTS

| | | |
|---|---|---|
| JP | 2004313124 A | 11/2004 |
| JP | 2009114125 A | 5/2009 |
| KR | 1020110021692 A | 3/2011 |
| WO | 0117494 A1 | 3/2001 |
| WO | 2009125944 A2 | 10/2009 |
| WO | 2012157921 A2 | 11/2012 |

OTHER PUBLICATIONS

Bodybuilding EGCG green tea extract for sale, 2010.*
Swanson Health Product EGCG green tea extract for sale, 2010.*
International Search Report with English Translation for International Application No. PCT/KR2013/011375 dated Mar. 12, 2014.
Written Opinion with English Translation for International Application No. PCT/KR2013/011375 dated Mar. 12, 2014.
Admire Dube et al., Effective use of reducing agents and nanoparticie encapsulation in stabilizing catechins in alkaline solution, Article, 2010, pp. 662-667, 122, Food Chemistry.
Ashok R. Patel et al., Novel polymer-polyphenol beads for encapsulation and microreactor applications, Journal, 2011, pp. 4294-4301, 7, Soft Matter, The Royal Society of Chemistry.
Chen Huangqin et al., Pilot study of the effect of green tea extractive epigallocatechin-3-gallate on degradation of collagen in dental erosion, 2012, pp. 549-551, vol. 30, No. 5, Database Medline.

(Continued)

*Primary Examiner* — Rei-Tsang Shiao
(74) *Attorney, Agent, or Firm* — Cantor Colburn, LLP

(57) ABSTRACT

Provide are a composition for forming a composite, the composition including a cellulose-based compound, a polyphenol-based compound, and a solvent, wherein an amount of the polyphenol-based compound is 1 to 40 parts by weight based on 100 parts by weight of the cellulose-based compound, a composite formed from the composition, and an orally ingestible composition including the composite. The composite has characteristics of being dissolved in a solvent in a various pH ranges depending on a mixing ratio of the cellulose-based compound and the polyphenol-based compound. Therefore, when the composite is used, a composite film may be easily prepared, and the composite film may be useful in medical or foods fields where film characteristics dependent on pH is required.

8 Claims, No Drawings

(56) References Cited

OTHER PUBLICATIONS

Panchuti Phoopuritham et al., Antioxidant Properties of Selected Plant Extracts and Application in Packaging as Antioxidant Cellulose-Based Films for Vegetable Oil, 2012, pp. 125-136, 25, Packaging Technology and Science, John Wiley & Sons, Ltd.

Q. Zhou et al., Investigating the Stability of EGCg in Aqueous Media, 2003, pp. 83-86, Current Separations.

Zhen-Yu Chen et al,, Stabilizing Effect of Ascorbic Acid on Green Tea Catechins, 1998, pp. 2512-2516, 46, American Chemicai Society.

Parietal Supplementary European Search Report for Application No. 13863023.1 mailed on May 10, 2016, citing the above reference(s).

* cited by examiner

COMPOSITION FOR FORMING COMPLEX, COMPLEX FORMED THEREFROM, AND COMPOSITION FOR ORAL ADMINISTRATION INCLUDING SAID COMPLEX

TECHNICAL FIELD

The inventive concept relates to a composition for forming a composite, a composite formed from the composition, and a composition including the composite, and more particularly, to a composition for forming a composite having pH dependent solubility, a composite formed from the composition, and an orally ingestible composition including the composite.

BACKGROUND ART

In the pharmaceutical or food field, film coating is used to acquire physical and chemical protection of active main components. Film coating in the pharmaceutical field is used to improve the quality of pharmaceutical products by protecting them from the environment, such as moisture, oxygen, or light and shielding the taste, smell, or color of active main components. Especially, film coating using a compound having acid resistance in a pH range of about 4 to 7 among compounds having pH-dependent dissolution characteristics increases resistance of a tablet against gastric juice, thereby rapidly initiating the release of the same in vivo intestinal environment. The film coating using a compound having pH-dependent dissolution characteristics as described above is called enteric coating.

If the enteric film coating is used in pharmaceutical materials, a compound, such as polymethacrylate, hydroxypropyl methylcellulose phthalate, polyvinylacrylate phthalate, cellulose acetate phthalate, or hydroxypropylmethylcellulose acetate succinate is used. And when the enteric film coating is used in some foods materials, alginates, shellac and the like are limitedly used. A film coating is formed by, for example, applying a composition containing the compound to a tablet, and drying the resultant to form a protective film.

However, the film described above, is impossible to use in some foods materials. Alginates or shellac that can be used for foods materials does not have sufficient pH dependent dissolution characteristics, thus dissolves slowly not only in the stomach but also in the intestine, not providing a satisfactory enteric quality that a user desires. In addition, there is much room for improvement for the pharmaceutical materials described above, as the pharmaceutical materials have low transparency from a quality point of view, and the pharmaceutical materials are brittle in a condition of low water concentration, and a large amount of additional excipients, such as plasticizer or talc should be used for sticky characteristics, or materials having phthalic acid have problems, such as formation of free phthalic acid.

DETAILED DESCRIPTION OF THE INVENTIVE CONCEPT

Technical Problem

The inventive concept provides a composition for forming a composite, a composite formed from the composition, and an orally ingestible composition including the composite.

Technical Solution

According to an aspect of the inventive concept, there is provided a composition for forming a composite including a cellulose-based compound, a polyphenol-based compound, and a solvent, wherein an amount of the polyphenol-based compound is 1 to 40 parts by weight based on 100 parts by weight of the cellulose-based compound.

According to another aspect of the inventive concept, there is provided a composite including a cellulose-based compound and a polyphenol-based compound, wherein an amount of the polyphenol-based compound is 1 to 40 parts by weight based on 100 parts by weight of the cellulose-based compound.

The composition for forming a composite may further include an antioxidant in an amount of 1 to 10 parts by weight based on 100 parts by weight of the cellulose-based compound.

According to another aspect of the inventive concept, there is provided an orally ingestible composition including the composite.

Advantageous Effects

The composite according to an exemplary embodiment of the present invention have no toxicity at all unlike conventional chemical materials, and does not produce any harmful material even when decomposed, and thus, freely available in any industrial field as foods materials. In addition, when applied in a human body, physiological functions, such as anti-oxidation function may be provided in the end, and antioxidant components of green tea or the like is in film layers, thereby preventing materials from being oxidized and protecting components inside films. Even on the process, additional chemical energy is not required due to simple dissolution and washing after reaction, and the like. Thus, it is very simple and environmentally friendly, with inexpensive process unit price. Additionally, antioxidants may be mixed to prevent a decrease in long-term stability and thereby improve long-term storage stability by about twenty times. In this regard, a decrease in long-term stability may occur by the interaction of natural products such as a polyphenol-based compound and a cellulose-based compound without the addition of antioxidants.

BEST MODE

Hereinafter, a composition for forming a composite, a composite formed from the composition, a method of preparing the same, and an orally ingestible composition including the same according to one or more exemplary embodiments of the present invention will be described.

The composition for forming a composite may include a cellulose-based compound, a polyphenol-based compound, and a solvent, wherein an amount of the polyphenol-based compound may be 1 to 40 parts by weight based on 100 parts by weight of the cellulose-based compound.

The solvent may include at least one selected from water and ethanol. An amount of the solvent may be 100 to 2000 parts by weight based on 100 parts by weight of a total amount of the cellulose-based compound and the polyphenol-based compound. When an amount of the solvent is within this range, components constituting the composition for forming a composite are uniformly mixed with each other, and thus, providing an excellent yield of the composite.

According to another aspect, there is provided a composite including a cellulose-based compound and a polyphenol-based compound, wherein an amount of the polyphenol-based compound may be 1 to 40 parts by weight based on 100 parts by weight of the cellulose-based compound.

An amount of the polyphenol-based compound may be, for example, 5 to 30 parts by weight based on 100 parts by weight of the cellulose-based compound.

When an amount of the polyphenol-based compound is less than 1 part by weight based on 100 parts by weight of the cellulose-based compound, the composite may not have pH selective or dependent solubility. When an amount of the polyphenol-based compound is more than 40 parts by weight based on 100 parts by weight of the cellulose-based compound, a composite film using the composite that is formed from the composition for forming a composite may be easily broken, and film-forming properties of the composite film may be reduced.

Polyphenols may typically be obtained from aerial parts of natural products and from various teas or fruits. The polyphenol-based compound is, for example, obtained from green tea extract.

Most components of the green tea extract used in the present invention are polyphenols excluding water, wherein the polyphenols are catechins, including epigallocatechin gallate (EGCG), epicatechin gallate (ECG), epicatechin (EC), and epigallocatechin (EGC). When including components similar to the components described above, the components may be used as polyphenol-based compounds.

Green tea extract may be obtained based on widely-known methods in the art, for example, by performing a process of extraction of green tea by using a mixed solvent of ethanol and water and drying by removing the solvent therefrom. The green tea extract obtained according to these methods may have, for example, a form of paste or powder.

An example of the polyphenol-based compound includes catechins.

The cellulose-based compound may include hydroxypropyl methylcellulose (HPMC), methylcellulose (MC), carboxymethylcellulose (CMC), a derivative thereof, or a mixture thereof.

In the HPMC, an amount of methoxy group is from 16.5 to 30.0 wt %, an amount of hydroxypropoxyl group is from 4 to 32 wt %, preferably, an amount of methoxy group is from 28 to 30 wt %, and an amount of hydroxypropoxyl group is from 7 to 12 wt %. When HPMC having such an amount of functional group is used, hydrophobic groups and hydrophilic groups in the HPMC are well balanced, and thus, the formation of the composite is easily carried out. Even after the formation of the composite, enteric coating film with an excellent film quality may be prepared due to excellent film-forming properties.

The composition for forming a composite and the composite formed from the composition may further include an antioxidant in an amount of 1 to 10 parts by weight based on 100 parts by weight of the cellulose-based compound. When an amount of the antioxidant is within this range, improving effect of long-term storage stability is excellent, and a film having an enteric function may be provided.

The antioxidant may further include ascorbic acid, butylhydroxyanisole, erythorbic acid, propyl gallate, rosemary oil, dibutyl hydroxy toluene, quercetin, tocopherol, or a mixture thereof.

The composite may further include a pH controlling agent.

The pH controlling agent is added to the composite while regulating the added amount so that the composite may dissolve in a target pH solution.

The pH controlling agent may include an alkaline agent.

Non-limiting examples of the alkaline agent includes sodium hydroxide, potassium hydroxide, calcium hydroxide, or a mixture thereof.

An amount of the pH controlling agent is 10 parts by weight or less, for example, from 0.01 to 7 parts by weight based on 100 parts by weight of the cellulose-based compound. When an amount of the pH controlling agent is within this range, turbidity and strength of a composite film formed by using the composite are excellent.

The composite according to an embodiment of the present invention uses only food materials that are safe to eat. The materials have a pH dependent solubility, and therefore, enteric properties equivalent to those of an enteric coating film material formed of pharmaceutical compounds, is obtained. Further, in addition to the antioxidant effect of the polyphenol, the composite may simultaneously have health benefits, and achieving a quality, overcoming inferior characteristics of pharmaceutical materials described above.

The composite according to an embodiment of the present invention is not limited to the above described general film coating and enteric coating, but may be applicable to any field requiring pH dependent dissolution characteristics. For example, in case that the composite is a material having characteristics of dissolving at pH 1 to 3 or more, the composite may be used as a common coating and a binder in which antioxidant property and functionality are implemented. In case that the composite is a material having characteristics of dissolving at pH 4 to 7 or more, the composite may be used as an enteric coating or enteric material as described above. Further, when the composite has characteristics of dissolving at pH 7 or more, the composite may be used as a sustained release coating base material, a sustained release filler, or a binder.

The composite has characteristics of being dissolved in a solvent, such as water in various pH ranges depending on a mixture ratio of the polyphenol-based compound and the cellulose-based compound. Further, when dissolved in some organic solvents, for example, a mixed solvent of ethanol and water at a weight ratio of 8:2, and followed by removing the solvent, the composite has excellent film-forming properties, and retain a nature of the original pH dependent solubility. Therefore, when the composite is used, a composite film may be easily prepared, and the composite film may be useful in medical or foods fields where film characteristics dependent on pH is required.

The composite may have, for example, excellent solubility characteristics with respect to a solvent in a pH range of 1.0 to 9.5. According to an exemplary embodiment, a soluble pH of the composite may be in a range of 4.0 to 7.0, more particularly, 5.0 to 5.5. The composite having such a soluble pH range may be used as an enteric coating or a base material for capsule.

The term "soluble pH" refers to a pH point where solubility of a composite drastically changes. For example, a composite having a soluble pH of 5 means that the composite does not dissolve at a pH less than 5, but dissolves at a pH 5 or more.

When the composite is used as an enteric coating or a base material for capsule, the composite containing composition may further include additives, such as a plasticizer, a lubricant, a coloring, a sunscreen, a solubilizing agent, a pH controlling agent, or a gelling agent.

Hereinafter, a method of preparing a composite using the composition for forming a composite and an orally ingestible composition using the composite will be described in detail. The method includes steps described below.

A first step is obtaining a composition for forming a composite by dissolving a polyphenol-based compound, a cellulose-based compound and optionally an antioxidant in a solvent.

The first step may include a process that is adding a polyphenol-based compound, a cellulose-based compound, and optionally an antioxidant to a solvent at the same time so as to dissolve the polyphenol-based compound, the cellulose-based compound and optionally the antioxidant in the solvent at the same time. Alternatively, the first step may include a process that is dissolving each of a polyphenol-based compound, a cellulose-based compound and optionally an antioxidant in a solvent so as to obtain a polyphenol-based compound solution, a cellulose-based compound solution and optionally an antioxidant solution, and then, mixing them with each other.

Non-limiting examples of the solvent includes at least one selected from water and ethanol. The solvent, for example, may be a mixed solvent of water and ethanol at a weight ratio of 5:5 to 2:8.

An amount of the solvent may vary due to viscosity difference depending on a molecular weight of the cellulose-based compound and the solvent may be used, for example, in a range of 100 to 2000 parts by weight based on 100 parts by weight of the total weight of the polyphenol-based compound, the cellulose-based compound and optionally the antioxidant. When an amount of the solvent is within this range, a composition for forming a composite in which the polyphenol-based compound, the cellulose-based compound and optionally the antioxidant are homogeneously dissolved in the solvent may be obtained.

A second step is drying the composition for forming a composite by removing the solvent therefrom, thereby obtaining the composite according to an exemplary embodiment of the present invention.

Drying the composition for forming a composite may be performed by using a method, such as evaporation under reduced pressure, spray drying, or natural drying.

The drying may be performed at 15 to 150° C., for example, at 50 to 60° C. When the drying is performed within this temperature range, the solvent may easily be removed without denaturation of the composite.

The composite obtained according to the above process may be washed with a solvent, in which the composite is not soluble, thereby unreacted materials or impurities being removed. When the washing step is performed, a high purity composite may be obtained.

The composite solvent, in which the composite is not soluble, may be any solvent having a pH that is smaller than a pH range dissolving a composite. Non-limiting examples of the composite solvent, in which the composite is not soluble, includes water without pH buffering capability.

According to another exemplary embodiment of the present invention, a composite may be obtained according to the method below.

Each of a polyphenol-based compound, a cellulose-based compound and optionally an antioxidant may be dissolved in water, that is, a solvent, and stirred each of them so as to obtain an aqueous polyphenol-based compound solution, an aqueous cellulose-based compound solution, and an aqueous antioxidant solution, respectively.

A pH controlling agent may further be added during the step of obtaining the aqueous polyphenol-based compound solution, the aqueous cellulose-based compound solution, and optionally the aqueous antioxidant solution. An amount and type of the pH controlling agent are the same as described above.

Thereafter, the aqueous polyphenol-based compound solution, the aqueous cellulose-based compound solution, and optionally the aqueous antioxidant solution may be mixed and stirred, and then these two materials or three materials react with each other so as to form a composite. The composite is obtained in a form of precipitate that does not dissolve in water. When drying the obtained precipitate, the composite may be obtained.

The drying may be performed at, for example, 15 to 90° C.

According to another embodiment of the present invention, there is provided an orally ingestible composition containing the composite.

The orally ingestible composition may be a formulation of a solid form, such as a tablet, a capsule, granules, or powder, or food, functional healthy food, or medicine.

An amount of the composite included in the orally ingestible composition may be 0.5 to 80 wt %. When an amount of the composite is within this range, an orally ingestible composition that provides an excellent physiological function may be obtained.

The orally ingestible composition may further include a pH controlling agent.

A type and amount of the pH controlling agent are the same as described above.

The orally ingestible composition may further include a solvent.

The solvent, for example, may include at least one selected from water and ethanol.

An amount of the solvent is not particularly limited; however, when the orally ingestible composition is directly used for coating, when a final viscosity of the orally ingestible composition is in a range of 500 cps or less, the coating process may be easily carried out.

The solvent, for example, is used in an amount of 100 to 2000 parts by weight based on 100 parts by weight of the total amount of the composite. The solvent, for example, includes a mixture of ethanol and water. A weight ratio of the water and ethanol is 5:5 to 2:8.

The composite of the present invention may alter a target soluble pH range depending on a mixing ratio of constituents. Accordingly, the composite may be applicable to various fields, such as to a binder or filler of a tablet, a coating of a capsule or tablet, or an enteric hard or soft capsule base material.

In addition, the composite has no toxicity and ensures safety by using vegetable raw materials, such as green tea extract, and may be variously used in foods and medicines, and it is advantageous that preparation cost is low due to a very simple preparation process. Alternatively, the composite may include the polyphenol-based compound so as to impart a physiological function, such as an antioxidant function or decrease in body fat, and may impart a function which prevents a coating core material from being oxidized.

Hereinafter, the present invention will be described in accordance with the Examples below; however, the present invention is not limited thereto.

Mode of the Inventive Concept

Green tea extract used in the following Examples is a paste obtained by extraction using ethyl alcohol as an organic solvent, followed by enrichment and drying of the same. An amount of the polyphenol-based compound contained in the green tea extract is about 60 parts by weight based on 100 parts by weight of the green tea extract.

In the polyphenol-based compound, catechins including epigallocatechingallate (EGCG) is in an amount of about 48 parts by weight based on 100 parts by weight of the polyphenol-based compound. Further, an amount of the EGCG contained in the catechins is about 34 parts by weight based on 100 parts by weight of catechins.

As for HPMC used in Examples below, HPMC2910 (AnyCoat-C® AN Grade) that is available from Samsung Fine Chemicals is used.

Examples 1 to 7

Preparation of Composite

As described in Table 1 below, a mixed solvent of water and ethanol were added to HPMC and green tea extract to obtain a composition for forming a composite. As described in Table 1 below, in Examples 1, 3 and 5 to 7, sodium hydroxide was additionally added to the composition for forming a composite. The green tea extract contains a polyphenol-based compound, and the polyphenol-based compound has a composition ratio EGCG:ECG:EC:EGC, based on weight, of 33.89:11.17:2.31:0.60.

An amount of the mixed solvent was controlled for a total amount of solid content (the HPMC and the green tea extract) in the composition for forming a composite to be about 15 parts by weight based on 100 parts by weight of the composition for forming a composite. An amount of ethanol was 80 wt %, and an amount of water was 20 wt % in the mixed solvent.

Thereafter, the solvent was removed by rotating the resultant in a rotary evaporator at 50 to 60° C., thereby obtaining a composite of HPMC and polyphenol-based compound.

TABLE 1

| Classification | HPMC (g) | Green tea extract (g) | Polyphenol-based compound (g) | Polyphenol-based compound with respect to 100 parts by weight of HPMC (Parts by weight) | Sodium hydroxide (g) |
|---|---|---|---|---|---|
| Example 1 | 0.65 | 0.30 | 0.18 | 27.55 | 0.05 |
| Example 2 | 0.70 | 0.30 | 0.18 | 25.58 | 0.00 |
| Example 3 | 0.80 | 0.15 | 0.09 | 11.11 | 0.05 |
| Example 4 | 0.87 | 0.13 | 0.08 | 9.30 | 0.00 |
| Example 5 | 0.68 | 0.30 | 0.18 | 26.52 | 0.02 |
| Example 6 | 0.82 | 0.15 | 0.09 | 11.17 | 0.03 |
| Example 7 | 0.81 | 0.16 | 0.10 | 11.87 | 0.03 |

Examples 8 to 15

Preparation of Composite

As described in Table 2 below, a mixed solvent of water and ethanol were added to HPMC, EGCG and ascorbic acid to obtain a composition for forming a composite. An amount of ethanol was 80 wt %, and an amount of water was amount 20 wt % in the mixed solvent.

Thereafter, the solvent was removed by rotating the resultant in a rotary evaporator at 50 to 60° C., thereby obtaining a composite of HPMC, EGCG, and ascorbic acid.

TABLE 2

| Classification | Amount | | | |
|---|---|---|---|---|
| | EGCG (g) | Ascorbic acid (g) | HPMC (g) | Mixed solvent (ml) |
| Example 8 | 0.5585 | 0.1379 | 9.31 | 100 |
| Example 9 | 0.5536 | 0.275 | 9.1796 | 100 |
| Example 10 | 0.6977 | 0.1733 | 9.1957 | 100 |
| Example 11 | 1.0873 | 0.5482 | 8.3674 | 100 |
| Example 12 | 1.1176 | 0.2716 | 8.5948 | 100 |
| Example 13 | 1.0083 | 0.1451 | 8.8468 | 100 |
| Example 14 | 1.1367 | 0.1151 | 8.7418 | 100 |
| Example 15 | 1.0998 | 0.381 | 8.5238 | 100 |
| Comparative Example 1 | 0 | 0 | 0 | 100 |

Example 16

Preparation of High Purity Composite 50 g of the composite obtained according to Example 7 above was added to 500 ml of purified water, in which a composite is not soluble, and the resultant was stirred for about 5 minutes.

The resultant was filtrated so as to obtain a solid, and the solid was dried in an oven at about 80° C., thereby obtaining a high purity composite including HPMC and a polyphenol-based compound from which impurities and unreacted materials have been removed.

Example 17

Preparation of Composite 2 g of HPMC was dissolved in 18 g of distilled water, thereby preparing 10 wt % aqueous HPMC solution. 20 g of the aqueous HPMC solution was strongly stirred with a homogenizer at about 4000 rpm, and 1.3 g of green tea extract paste was slowly added dropwise thereto so as to form a precipitate.

The resultant was filtrated to separate the precipitate, and was dried in an oven at 80° C., thereby obtaining a composite containing HPMC and polyphenol-based compound.

Preparation Examples 1 to 15

Preparation of Composite Film 1 g of the composite prepared according to each of Examples 1 to 15 was dissolved in 5 ml of 80 wt % aqueous ethanol solution, thereby a preparing composite solution. The composite solution was cast and natural-dried, thereby obtaining a composite film having a thickness of about 60 μm. In this case, the composite film in Preparation Example n (n=1~15) was prepared using the composite in Example n (n=1~15). In the present specification, "natural-drying" means drying overnight at room temperature (about 25° C.).

Comparative Preparation Example 1

10 g of HPMC was dissolved in 100 ml of 80 wt % aqueous ethanol solution, thereby preparing a HPMC solution. The HPMC solution was cast and natural-dried, thereby obtaining a HPMC film having a thickness of about 60 μm.

Evaluation Example 1

Brittleness Comparison

The composite films obtained according to Preparation Examples 1 to 7 and the HPMC film in Comparative Preparation Example 1 were physically perforated to produce 10 circular perforations each having a diameter of about 6 mm at room temperature condition and brittlenesses of the films were evaluated according to the degree of damage of the circular films produced as a result of the perforating. Here, "room temperature condition" means that a film is put in an airtight container and then the container is stored in a thermo-hygrostat maintaining a temperature of 25° C. and a relative humidity of 50% therein.

⊚: In the case that 10 circular films that had been separated from the film maintained a circular form
○: In the case that 8 to 9 circular films of 10 circular films that had been separated from the film maintained a circular form
×: In the case that 3 or more circular films of 10 circular films that had been separated from the film were damaged The results of brittleness evaluation of the films are as shown in Table 3.

Evaluation Example 2

Film Turbidity

Film turbidities of the films obtained according to Preparation Examples 1 to 7 and the HPMC film of Comparative Preparation Example 1 were evaluated by visually observing transparencies of the films.
⊚: In the case that a film is transparent:
○: In the case that a part of a film is blurred
×: In the case that a film is blurred as a whole
The results of turbidity evaluation of the films are shown in Table 3.

Evaluation Example 3

Soluble pH

Soluble pH of the composite films obtained according to Preparation Examples 1 to 7 and the HPMC film of Comparative Preparation Example 1 were investigated by adding the films in to a Britton-Robinson buffer and stirring the resulting mixture at about 37° C. for 1 hour.

The Britton-Robinson buffer was prepared by mixing 2.5 mL of glacial acetic acid with 2.7 mL of 99.9 wt % phosphoric acid and 2.47 g of boric acid, adding purified water thereto so as to amount to 1000 mL, and dropwisely adding 2N sodium hydroxide solution thereto.

By adjusting an amount of the dropwisely added 2N sodium hydroxide solution, Britton-Robinson buffers having various pH ranges were prepared.

Soluble pH ranges of the films were investigated, and the results are shown in Table 3.

TABLE 3

| Classification | Brittleness | Film turbidity | Soluble pH |
|---|---|---|---|
| Preparation Example 1 | ○ | ○ | 7.00 |
| Preparation Example 2 | ○ | ⊚ | 9.25 |
| Preparation Example 3 | ⊚ | ○ | 1.00 |
| Preparation Example 4 | ⊚ | ⊚ | 8.00 |
| Preparation Example 5 | ⊚ | ⊚ | 8.00 |
| Preparation Example 6 | ○ | ○ | 5.00 |
| Preparation Example 7 | ○ | ○ | 5.50 |
| Comparative Preparation Example 1 | ⊚ | ⊚ | 1.00 or less |

By referring to Table 3, it was found that the composite films of Preparation Examples 1 to 7 have moderate or high brittleness and turbidity. Further, it was verified that the composite films of Preparation Examples 1 to 7 have various soluble pH ranges depending on amounts of green tea extract, HPMC, and sodium hydroxide, unlike the HPMC film of Comparative Preparation Example 1.

Evaluation Example 4

Evaluation of Long-Term Storage Stability of Composite Film

The composite films obtained according to Preparation Examples 8 to 15 and the HPMC film of Comparative Preparation Example 1 were long-term stored under a room temperature condition and an acceleration condition, and then, EGCG reduction ratios, pH dependent dissolution characteristics, and brittlenesses were evaluated. The results thereof are shown in Table 4 and 5 below, respectively. Table 4 shows evaluation results, after storing the composite films under a room temperature condition or acceleration condition for 10 weeks, and Table 5 shows evaluation results, after storing the composite films under a room temperature condition or acceleration condition for 18 weeks. In the present specification, a "room temperature condition" means that a composite film is put in an airtight container and then the container is stored in a thermo-hygrostat maintaining a temperature of 25° C. and a relative humidity of 50% therein, and an "acceleration condition" means that a composite film is put in an airtight container and then the container is stored in a thermo-hygrostat maintaining a temperature of 40° C. and a relative humidity of 75% therein.

(EGCG Reduction Ratio Evaluation)

200 mg of each of a film before being stored and the film being stored under a room temperature condition or acceleration condition were collected, dissolved in 10 ml of a mixture solution of 60 volume % of methanol and 40 volume % of water, and pretreated with a syringe filter of 0.45 um, thereby preparing a sample solution. Then, the sample solution was quantified by using a high-performance liquid chromatography (HPLC). A stainless steel pipe having an inner diameter of 4.6 mm and length of 250 mm, which is filled with 5 μm octadecylsilanized silica gel, was used as HPLC column. A mixed solution of water:methanol (at 95:5, based on weight ratio) and a mixed solution of acetonitrile:methanol (at 95:5, based on weight ratio) were used as a mobile phase. The flow rate was 0.8 ml/min, UV/visible light detector was used to analyze the sample solution at 278 nm, and a temperature of the sample solution and the column was 25° C. The sample solution injection volume was 30 μl. The collected solution was analyzed with HPLC to measure EGCG amount. Later, EGCG reduction ratio was obtained on the basis of the following Equation 1.

EGCG reduction ratio (wt %)=(EGCG amount before being stored−EGCG amount while being stored)/(EGCG amount before being stored)*100  [Equation 1]

(pH Dependent Dissolution Characteristics Evaluation)

pH dependent dissolution characteristics were evaluated in the same manner, using the same device and method used in Evaluation Example 2 to measure "soluble pH". However, "pH dependent dissolution characteristics" was classified as ○ in case that a film dissolved at pH 6.8 and was not dissolved at pH 1.2, and as × in other cases.

(Film Brittleness)

Brittlenesses of films were evaluated in the same manner as in Evaluation Example 1 above.

TABLE 4

| | Classification | | | | | |
|---|---|---|---|---|---|---|
| | 10 weeks under room temperature condition | | | 10 weeks under acceleration condition | | |
| | EGCG reduction ratio (wt %) | pH dependent dissolution characteristics | Film brittleness | EGCG reduction ratio (wt %) | pH dependent dissolution characteristics | Film brittleness |
| Preparation Example 8 | 7.6 | ○ | ◉ | 24.3 | ○ | ◉ |
| Preparation Example 9 | 3.3 | ○ | ◉ | 28.1 | ○ | ◉ |
| Preparation Example 10 | 8.6 | ○ | ◉ | 24.9 | ○ | ◉ |
| Preparation Example 11 | 0.1 | ○ | ○ | 13.4 | ○ | ○ |
| Preparation Example 12 | 9.7 | ○ | ○ | 22.2 | ○ | ○ |
| Preparation Example 13 | 13.4 | ○ | ◉ | 15.1 | ○ | ◉ |
| Preparation Example 14 | 5.2 | ○ | ○ | 17.2 | ○ | ○ |
| Preparation Example 15 | 6.7 | ○ | ○ | 27.4 | ○ | ○ |
| Comparative Preparation Example 1 | — | X | ◉ | — | X | ◉ |

Referring to Table 4, when stored for 10 weeks, it was found that the composite films prepared in Preparation Examples 8 to 15 have excellent pH dependent dissolution characteristics compared to the HPMC film of Comparative Preparation Example 1. In addition, it was shown that EGCG reduction ratios of the composite films prepared in Preparation Examples 8 to 15 were 14 wt % or less when stored for 10 weeks at room temperature, and EGCG reduction ratios thereof were 30 wt % or less when stored for 10 weeks under an acceleration condition. Further, film brittlenesses of the composite films prepared in Preparation Examples 8 to 15 were moderate or high when stored for 10 weeks.

TABLE 5

| | Class | | | | | |
|---|---|---|---|---|---|---|
| | 18 weeks under room temperature condition | | | 18 weeks under acceleration condition | | |
| | EGCG reduction ratio (wt %) | pH dependent dissolution characteristics | Film brittleness | EGCG Reduction ratio (wt %) | pH dependent dissolution characteristics | Film brittleness |
| Preparation Example 8 | 8.80 | ○ | ◉ | 23.90 | ○ | ◉ |
| Preparation Example 9 | 11.00 | ○ | ◉ | 34.40 | ○ | ◉ |

TABLE 5-continued

| | Class | | | | | |
|---|---|---|---|---|---|---|
| | 18 weeks under room temperature condition | | | 18 weeks under acceleration condition | | |
| | EGCG reduction ratio (wt %) | pH dependent dissolution characteristics | Film brittleness | EGCG Reduction ratio (wt %) | pH dependent dissolution characteristics | Film brittleness |
| Preparation Example 10 | 12.10 | ○ | ◉ | 26.00 | ○ | ◉ |
| Preparation Example 11 | 2.70 | ○ | X | 21.40 | X | X |
| Preparation Example 12 | 16.50 | ○ | X | 27.20 | ○ | X |
| Preparation Example 13 | 10.20 | X | ◉ | 21.80 | X | ◉ |
| Preparation Example 14 | 7.00 | ○ | X | 17.20 | ○ | X |
| Preparation Example 15 | 11.50 | ○ | X | 35.20 | ○ | X |
| Comparative Preparation Example 1 | — | X | ◉ | — | X | ◉ |

Referring to Table 5, when stored for 18 weeks, EGCG reduction ratios, pH dependent dissolution characteristics, and brittlenesses of the composite films prepared in Preparation Examples 8 to 15 were found to vary depending on a composition.

Examples 18 to 24

Preparation of HPMC-EGCG Composite Including Other Antioxidant

Composites were prepared in the same manner as in Example 8, except that other antioxidants listed in Table 6 were used instead of ascorbic acid. The composite of Example n (n=18~24) was used to prepare a composite film of Preparation Example n(n=18~24) in Table 6 below.

Example 25

Preparation of HPMC-EGCG Composite Including Ascorbic Acid

A composite was prepared in the same manner as in Example 8. The composite of Example 25 was used to prepare a composite film of Preparation Example 25 in Table 6 below.

Example 26

Preparation of HPMC-EGCG Composite Not Including Antioxidant

A composite was prepared in the same manner as in Example 8, except that ascorbic acid was not used. The composite of Example 26 was used to prepare a composite film of Preparation Example 26 in Table 6 below.

Preparation Examples 18 to 26

Preparation of Composite Film 10 g of the composite according to Examples 18 to 26 was dissolved in 100 ml of 80 wt % aqueous ethanol solution, thereby preparing a composite solution. The composite solution was cast and natural-dried, thereby obtaining a composite film having a thickness of about 60 μm.

Evaluation Example 5

Evaluation of Long-Term Storage Stability of Composite Film

The composite films obtained according to Preparation Examples 18 to 26 were stored under a room temperature condition for 14 weeks and an acceleration condition for 14 weeks, and then, EGCG reduction ratios and pH dependent dissolution characteristics were evaluated. The results thereof are shown in Table 6 below.

TABLE 6

| Classification | Antioxidant | 14 weeks under room temperature condition | | 14 weeks under acceleration condition | |
|---|---|---|---|---|---|
| | | EGCG reduction ratio (wt %) | pH dependent dissolution characteristics | EGCG reduction ratio (wt %) | pH dependent dissolution characteristics |
| Preparation Example 18 | Propyl Gallate | 0.12 | ○ | 0.92 | ○ |
| Preparation Example 19 | Rosemary oil | 1.29 | ○ | 5.81 | ○ |

TABLE 6-continued

| Classification | Antioxidant | 14 weeks under room temperature condition | | 14 weeks under acceleration condition | |
|---|---|---|---|---|---|
| | | EGCG reduction ratio (wt %) | pH dependent dissolution characteristics | EGCG reduction ratio (wt %) | pH dependent dissolution characteristics |
| Preparation Example 20 | Butylhydroxy anisole | 0.98 | ○ | 10.88 | ○ |
| Preparation Example 21 | Erythorbic acid | 7.99 | ○ | 13.57 | ○ |
| Preparation Example 22 | Dibutyl hydroxy toluene | 6.76 | ○ | 10.58 | ○ |
| Preparation Example 23 | Quercetin | 5.19 | ○ | 9.13 | ○ |
| Preparation Example 24 | Tocopherol | 4.79 | ○ | 12.24 | ○ |
| Preparation Example 25 | Ascorbic acid | 7.90 | ○ | 19.60 | ○ |
| Preparation Example 26 | Not added | 10.80 | ○ | 23.60 | ○ |

Referring to Table 6, it was found that the composite films prepared in Preparation Examples 18 to 25, to which antioxidants were added, from among the composite films prepared in Preparation Examples 18 to 26 showed highly increased EGCG long-term storage stability compared to the composite film prepared in Preparation Example 26, to which an antioxidant was added.

Preparation Example 27

Gelatin Capsule Coating Using Composite 9.5 g of HPMC and 0.5 g of EGCG were dissolved in 150 ml of a mixed solvent of 80 wt % of ethanol and 20 wt % of water, thereby preparing a composite coating solution. The composite coating solution was coated on a soft gelatin capsule (Chong Kun Dang Healthcare Corp., Well-being Omega 3 1000 mg soft capsule) by using a coater (Freund, Hi-coater) under a condition of an exhaust air temperature of 45° C., an intake air temperature of 35° C., a feed rate of the composite coating solution of 3 g/min, an in air flow of 0.8 m³/min, a pan static of −20 Pa, a pan speed of 13 rpm, and a spray air pressure of 0.2 MPa. The coating was performed until an amount of coating became 20 wt % compared to 100 wt % of the soft gelatin capsule before the coating.

Comparative Preparation Example 2

Gelatin Capsule Coating Using HPMC 10 g of HPMC was dissolved in 150 ml of a mixed solvent of 80 wt % of ethanol and 20 wt % of water, thereby preparing a coating solution. The coating solution was coated on a soft gelatin capsule (Chong Kun Dang Healthcare Corp., Well-being Omega 3 1000 mg soft capsule) by using a coater (Freund, Hi-coater) under the same condition as that of Preparation Example 27. The coating was performed until an amount of coating became 20 wt % compared to 100 wt % of the soft gelatin capsule before the coating.

Evaluation Example 6

Disintegration Comparison in Artificial Gastric Juice (pH 1.2) and Artificial Enteric Juice (pH 6.8)

Disintegration properties depending on pH of the coated soft gelatin capsules in Preparation Example 27 and Comparative Preparation Example 2 were comparatively evaluated as follows. That is, a dissolution test was performed according to a disintegration test method of Korean Pharmacopoeia (9th edition) at a temperature of 37° C. 900 ml of each of an artificial gastric juice (pH 1.2, hydrochloride buffer solution) and an artificial enteric juice (pH 6.8, 50 mM phosphate buffer solution) were used as eluant. A disintegration test began in artificial gastric juice of pH 1.2. 2 hours later, the artificial gastric juice in a disintegrator was substituted with artificial enteric juice of pH 6.8, and was subjected to further disintegrate for one more hour, and disintegration times of 6 capsules were measured.

As a result of the disintegration test, an average disintegration time of the capsule of Preparation Example 27 was 2 hours and 20 minutes, and an average disintegration time of the capsule of Comparative Preparation Example 2 was 40 minutes. It was found that in the case of the capsule of Comparative Preparation Example 2, as the capsule does not have pH dependent dissolution characteristics, the capsule is easily disintegrated in the artificial gastric juice of pH 1.2; however, in the case of the capsule of Preparation Example 27, the capsule did not disintegrated in the artificial gastric juice of pH 1.2 for 2 hours and came to disintegrate after being moved to the artificial enteric juice of pH 6.8.

While the inventive concept has been particularly shown and described with reference to exemplary embodiments thereof, it will be understood that various changes in form and details may be made therein without departing from the spirit and scope of the following claims.

The invention claimed is:

1. A composition for forming a composite, the composition comprising:
a cellulose-based compound,
a polyphenol-based compound,
an antioxidant selected from ascorbic acid, butylhydroxyanisole, erythorbic acid, propyl gallate, rosemary oil, dibutyl hydroxy toluene, quercetin, tocopherol, or a mixture thereof, in an amount of 1 to 10 parts by weight based on 100 parts by weight of the cellulose-based compound, and
a solvent,
wherein an amount of the polyphenol-based compound is 1 to 7.59 parts by weight based on 100 parts by weight of the cellulose-based compound, wherein the cellulose-based compound is hydroxypropyl methylcellulose (HPMC), methylcellulose (MC), carboxymethylcellulose (CMC), a derivative thereof, or a mixture thereof, wherein the polyphenol-based compound is selected from epigallocatechin gallate (EGCG), epicatechin gallate (ECG), epicatechin (EC), and epigallocatechin (EGC).

2. The composition of claim 1, wherein the polyphenol-based compound is obtained from green tea extract.

3. The composition of claim 1, wherein the solvent comprises at least one selected from water and ethanol, wherein an amount of the solvent is 100 to 2000 parts by weight based on 100 parts by weight of a total amount of the cellulose-based compound and the polyphenol-based compound.

4. The composition of claim 1, the composition further comprising a pH controlling agent.

5. The composition of claim 4, wherein the pH controlling agent is an alkaline agent comprising sodium hydroxide, potassium hydroxide, calcium hydroxide, or a mixture thereof.

6. A composite comprising
a cellulose-based compound,
a polyphenol-based compound, and
an antioxidant selected from ascorbic acid, butylhydroxyanisole, erythorbic acid, propyl gallate, rosemary oil, dibutyl hydroxy toluene, quercetin, tocopherol, or a mixture thereof, in an amount of 1 to 10 parts by weight based on 100 parts by weight of the cellulose-based compound,
wherein an amount of the polyphenol-based compound is 1 to 7.59 parts by weight based on 100 parts by weight of the cellulose-based compound,
wherein the cellulose-based compound is hydroxypropyl methylcellulose (HPMC), methylcellulose (MC), carboxymethylcellulose (CMC), a derivative thereof, or a mixture thereof,
wherein the polyphenol-based compound is selected from epigallocatechin gallate (EGCG), epicatechin gallate (ECG), epicatechin (EC), and epigallocatechin (EGC).

7. The composite of claim 6, wherein the composite has a pH dependent solubility.

8. An orally ingestible composition comprising the composite of claim 6.

* * * * *